United States Patent
Mihalik et al.

(10) Patent No.: US 9,168,093 B2
(45) Date of Patent: Oct. 27, 2015

(54) COOLING SYSTEMS FOR ELECTRODE ARRAYS

(75) Inventors: Teresa Ann Mihalik, Montreal (CA); Alexander J. Asconeguy, Murrieta, CA (US); Ricardo D. Roman, Chula Vista, CA (US); Timothy J. Corvi, Carlsbad, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 844 days.

(21) Appl. No.: 13/428,051

(22) Filed: Mar. 23, 2012

(65) Prior Publication Data
US 2012/0245577 A1    Sep. 27, 2012

Related U.S. Application Data
(60) Provisional application No. 61/467,446, filed on Mar. 25, 2011.

(51) Int. Cl.
*A61B 18/14* (2006.01)
*A61B 18/00* (2006.01)

(52) U.S. Cl.
CPC ..... *A61B 18/1492* (2013.01); *A61B 2018/0016* (2013.01); *A61B 2018/00029* (2013.01); *A61B 2018/00214* (2013.01); *A61B 2018/00577* (2013.01); *A61B 2018/1435* (2013.01); *A61B 2018/1467* (2013.01); *A61B 2218/002* (2013.01)

(58) Field of Classification Search
CPC .............................. A61B 18/1492; A61B 18/00
USPC ................................................ 606/32–34, 41
See application file for complete search history.

(56) References Cited

U.S. PATENT DOCUMENTS

| | | | |
|---|---|---|---|
| 5,863,291 | A | 1/1999 | Schaer |
| 5,906,613 | A | 5/1999 | Mulier et al. |
| 2002/0004644 | A1 | 1/2002 | Koblish |
| 2003/0204183 | A1 | 10/2003 | Natale |
| 2004/0143256 | A1 | 7/2004 | Bednarek |
| 2004/0167509 | A1 | 8/2004 | Taimisto |
| 2006/0287650 | A1 | 12/2006 | Cao et al. |
| 2011/0028962 | A1 | 2/2011 | Werneth et al. |

FOREIGN PATENT DOCUMENTS

| | | |
|---|---|---|
| CN | 101309651 A | 11/2008 |
| CN | 101969875 A | 2/2011 |

(Continued)

OTHER PUBLICATIONS
International Search Report.
(Continued)

*Primary Examiner* — Deborah Malamud
(74) *Attorney, Agent, or Firm* — Christopher & Weisberg, P.A.

(57) ABSTRACT

A medical device is disclosed, including a catheter body; an electrode array coupled to the catheter body, the electrode array being transitionable from a substantially linear configuration to a substantially helical configuration; and a fluid conduit coupled to the catheter body spaced apart from the electrode array, wherein the fluid conduit is transitionable from a substantially linear configuration to a substantially helical configuration. The device may include a fluid source in communication with the fluid conduit and a radiofrequency signal generator coupled to the electrode array.

16 Claims, 9 Drawing Sheets

(56) References Cited

FOREIGN PATENT DOCUMENTS

| | | |
|---|---|---|
| DE | 9209100 U1 | 11/1993 |
| WO | 03094764 A1 | 11/2003 |
| WO | 2004100813 A2 | 11/2004 |
| WO | 2009/137924 A1 | 11/2009 |

OTHER PUBLICATIONS

The State Intellectual Property Office of the People's Republic of China, Notice on the First Office Action and Search Report, Application/Patent No. 201280014678.4, Applicant: Medtronic Ablation Frontiers LLC, Title: Cooling Systems for Electrode Arrays, Apr. 24, 2015, 16 pages (English translation).

Section A-A

COOLING SYSTEMS FOR ELECTRODE ARRAYS

CROSS-REFERENCE TO RELATED APPLICATION

This application is related to and claims priority to U.S. Provisional Patent Application Ser. No. 61/467,446, filed Mar. 25, 2011 entitled COOLING SYSTEMS FOR ELECTRODE ARRAYS, the entirety of which is incorporated herein by reference.

STATEMENT REGARDING FEDERALLY SPONSORED RESEARCH OR DEVELOPMENT n/a

FIELD OF THE INVENTION

The present invention relates to systems and methods of use thereof for controlling temperature of medical devices, and in particular, toward cooling electrodes or other thermally-active treatment component.

BACKGROUND OF THE INVENTION

Minimally invasive devices are often employed for medical procedures, including those involving ablation, dilation, and the like. In a particular situation, an ablation procedure may involve creating a series of inter-connecting or otherwise contiguous lesions in order to electrically isolate tissue believed to be the source of an arrhythmia. Such lesions may be created using a variety of different energy transmission modalities, such as cryogenic freezing or heating with radiofrequency ("RF") energy, for example.

Radiofrequency or other ablation devices often include one or more electrically conductive surfaces or electrodes to impart electrical or thermal energy conduction through a tissue site. During operation, the tissue heats up, thus heating the electrodes that are in tissue contact. Exceeding a particular temperature range or threshold can result in unwanted injury to the tissue site, including tissue charring or coagulum formation, and can also compromise the medical device itself.

In view of the above, it is desirable to provide effective cooling mechanisms for thermal or electrical devices to avoid excessive heating and associated unwanted injury to the patient.

SUMMARY OF THE INVENTION

The present invention provide effective cooling mechanisms for thermal or electrical devices to avoid excessive heating and associated unwanted injury to the patient. For example, a medical device is provided, including a catheter body; an electrode array coupled to the catheter body, the electrode array being transitionable from a substantially linear configuration to a substantially helical configuration; and a fluid conduit coupled to the catheter body spaced apart from the electrode array, wherein the fluid conduit is transitionable from a substantially linear configuration to a substantially helical configuration. The fluid conduit may be releasably coupled to the catheter body. The fluid conduit may be transitionable from a substantially linear configuration to a substantially helical configuration independently of the electrode array. The fluid conduit may include a plurality of apertures and/or be attached to the electrode array by a plurality of connectors. The plurality of connectors may be thermally conductive. The device may include a shaft movably coupled to the catheter body, where a proximal portion of the electrode array is attached to the catheter body and a distal portion of the electrode array is attached to the shaft. A proximal portion of the fluid conduit may be attached to the catheter body and a distal portion of the fluid conduit may be attached to the shaft. The fluid conduit may extend from a distal end of the shaft. The device may include a fluid supply in fluid communication with the fluid conduit and/or a radiofrequency signal generator in communication with the electrode array.

A medical device is also disclosed, including a catheter body; an electrode array coupled to the catheter body, the electrode array including a plurality of electrodes and being transitionable from a substantially linear configuration to a substantially helical configuration; and a fluid conduit passing through each of the plurality of electrodes. Each of the plurality of electrodes may be mounted on a carrier arm, and the fluid conduit may be adjacent to the carrier arm. The fluid conduit may define a plurality of apertures, where each aperture is positioned proximate to each of the plurality of electrodes. The fluid conduit may be at least partially disposed within the carrier arm. Each electrode may define a single passage therethrough, or may define a plurality of passages therethrough. The fluid conduit may define a first portion and a second portion, where the second portion is coiled around the first portion and/or the second portion may define a plurality of openings positioned to disperse fluid onto the first portion.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1A:
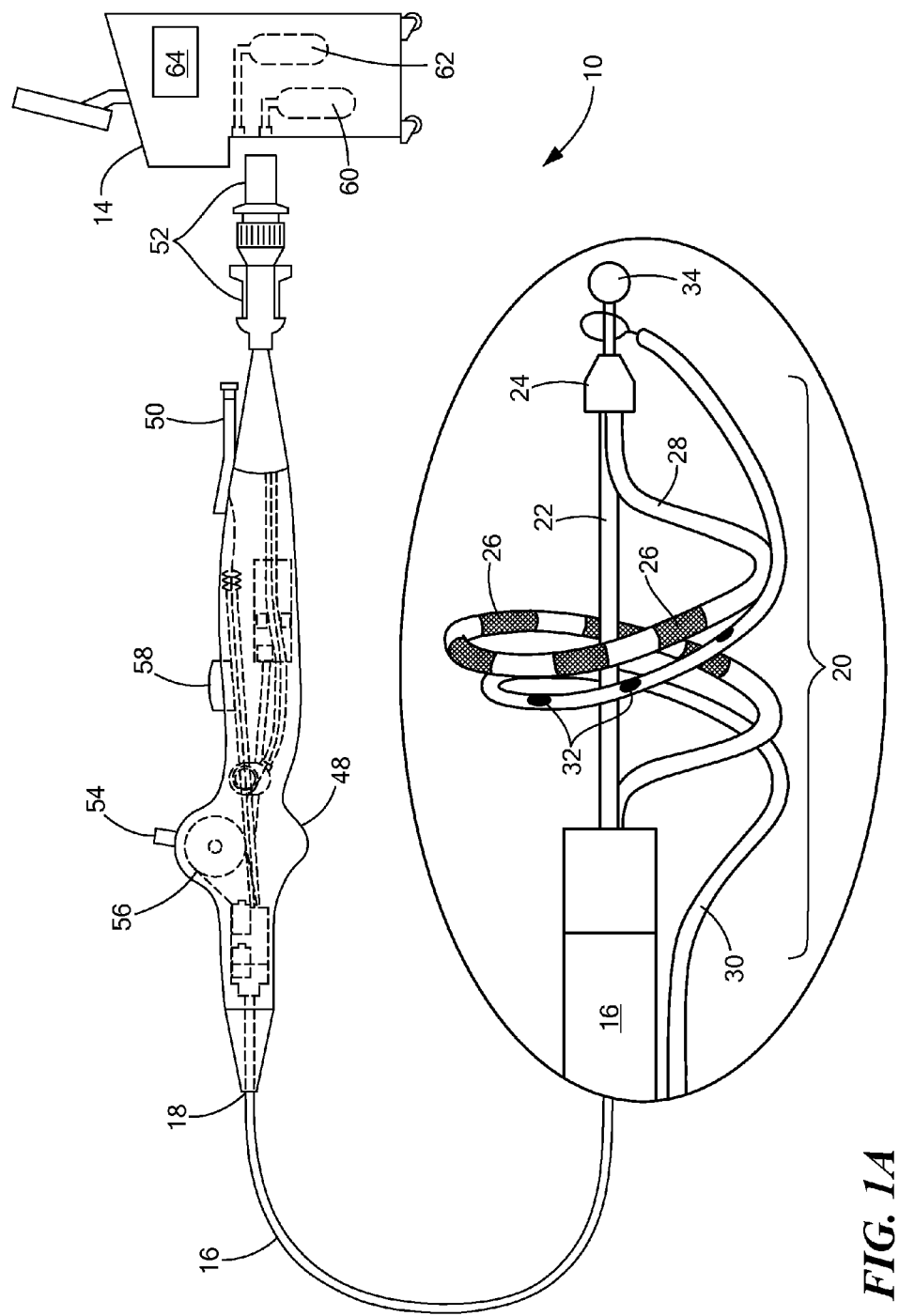
FIG. 1A is an illustration of an example of a medical system constructed in accordance with the principles of the present invention.

The present invention disclosure advantageously provides effective cooling mechanisms and uses thereof for thermal or electrical devices to avoid excessive heating and associated unwanted injury to the patient. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more diagnostic or treatment regions for energetic, therapeutic and/or investigatory interaction between the medical device 12 and a treatment site. The treatment region(s) may deliver, for example, cryogenic therapy, radiofrequency energy, electroporation treatment or other energetic transfer with a tissue area in proximity to the treatment region(s), including cardiac tissue, tumors, or other undesired growths or structures.

Figure 1B:
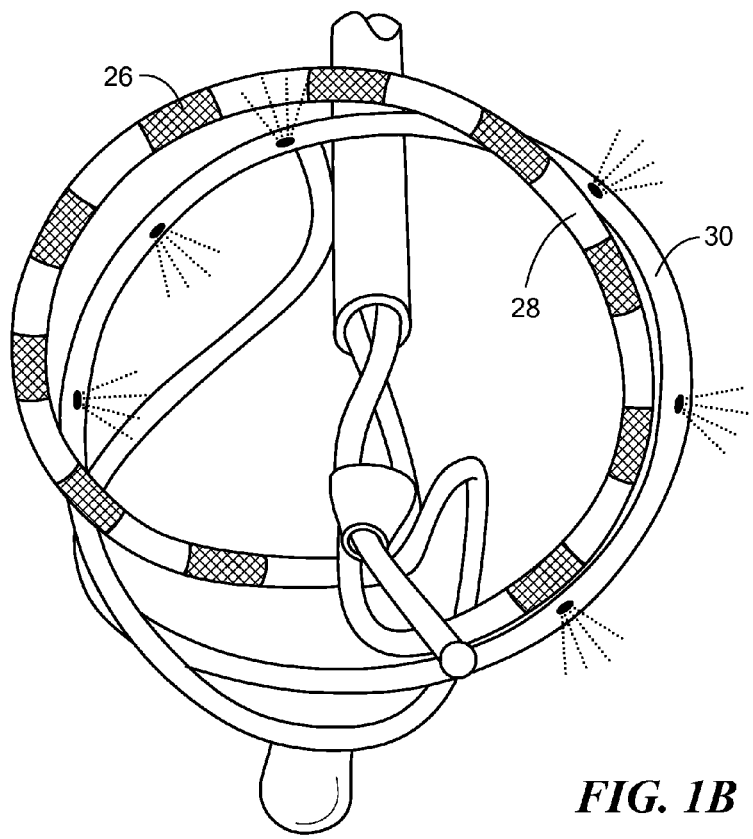
FIG. 1B is an alternative view of the system of FIG. 1A.

Continuing to refer to FIGS. 1A-1B, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion 18 of the elongate body 16 and the distal portion 20 of the elongate body 16, as discussed in more detail below.

The medical device 12 may include a shaft 22 at least partially disposed within a portion of the elongate body 16. The shaft 22 may extend or otherwise protrude from a distal end of the elongate body 16, and may be movable with respect to the elongate body 16 in longitudinal and rotational directions. That is, the shaft 22 may be slidably and/or rotatably moveable with respect to the elongate body 16. The shaft 22 may further define a lumen therein for the introduction and passage of a guide wire. The shaft 22 may include or otherwise be coupled to a distal tip 24 that defines an opening and passage therethrough for the guide wire. The distal tip 24 may be constructed from an electrically conductive material and used for mapping, pacing, ablating or otherwise electrically interacting with a targeted tissue region.

The distal portion 20 provides for the treatment, monitoring, and/or otherwise clinically interacting with a desired tissue region, such as the heart. The distal portion 20 may include, for example, an electrode array including a plurality of electrodes 26 disposed near, on, or substantially on the distal end of the elongate body 16. These electrodes 26 may be mounted to detect electrical signals between any pair of electrodes (bi-pole) for mapping of electrical activity, and/or for performing other functions such as pacing of the heart. Moreover, the electrodes 26 may deliver ablation energy across an electrode pair or from independent electrodes when delivering monopolar energy. In a particular example, the plurality of electrodes may include from four (4) to sixteen (16) electrodes with symmetric or asymmetric spacing. The electrodes 26 may be constructed from platinum, iridium, gold, silver or the like, and may measure approximately about 3 mm in length and separated by a distance of approximately 1 mm to approximately 4 mm, for example.

The medical device 12 may further include one or more temperature sensors (not shown) proximate the distal portion 20 and/or electrodes 26 for monitoring, recording or otherwise conveying measurements or conditions within the medical device 12, the ambient environment at the distal portion 20 of the medical device 12, and/or an interface or junction between the device and a contacted tissue surface. Each electrode 26 may include an integral thermocouple (not shown) or sensor located on or near the tissue side of the electrode to monitor the temperature at each ablation site before and during ablation. For example, the temperature sensor(s) may include a thermistor directly coupled to one or more of the electrodes 26; may also be positioned adjacent an electrode 26 at the distal portion 20 of the medical device 12, and/or may be embedded into a surface of the elongate body 16, for example. The sensor(s) may be in communication with the control unit 14 for initiating or triggering one or more alerts or therapeutic delivery modifications during operation of the medical device 12.

The electrode array may be arranged in a resiliently biased manner and have specific geometric configurations which generally allow them to ablate specific tissue (such as a pulmonary vein, for example) having predetermined or otherwise known geometric or topographical characteristics. The electrode array may be selectively movable from a primary, stored or delivery configuration for transport and delivery to the treatment site (such as a radially constrained configuration) to multiple secondary, deployed or expanded configurations for treatment (having helical, coiled, arcuate, or other geometric configurations).

Continuing to refer to FIGS. 1A-1B, the distal portion 20 of the medical device 12 may include a carrier assembly that supports the electrodes 22 thereon. The carrier assembly may include a flexible carrier arm 28 having one end coupled to the elongate body 16, and an opposite end coupled to the distal tip 24. The distal tip 24 may define a lumen for receiving and/or coupling to a portion of the carrier arm. The carrier arm 28 may be constructed from a shape memory material, such as nitinol, to provide one or more pre-determined and/or biased geometric configurations. Conventional marking elements (e.g. radiopaque markers) may be included in the distal treatment assembly, carrier assemblies or other components of the medical device to determine the relative location of the carrier assembly and/or the deployment condition of the carrier assembly, as well as confirm contact with tissue.

As the carrier assembly is coupled to the distal end of the shaft 22 by the distal tip 24, the shaft 22 can be manipulated to control the geometry of the carrier assembly and thus the electrode array. For example, the shaft 22 can be retracted to transition the carrier arm 28 from a near linear configuration to a partial circumferential (less than 360.degree.) loop (i.e., a partial helical or spiral shape). Advancement and/or retraction of the shaft 22 can adjust the geometry of the loop of the electrode array, such as increasing/decreasing the diameter of the carrier arm 28. Moreover, rotation of the shaft 22 can also increase and decrease the diameter of the carrier arm 28, and thus the electrode array.

The carrier assembly may include reinforcement elements or otherwise be constructed to provide desired degrees of stiffness, flexibility, and/or torque transmission along its length or at discrete locations along the length thereof. For example, the carrier arm 28 may include wires, braiding, increased wall-thickness, additional wall layering, sleeves, or other components reinforcing or otherwise supplementing an outer wall or thickness at the junction or region in proximity to the distal tip 24 to minimize the likelihood of structural failure resulting from the experienced torque or strain transmitted from the shaft 22 through the distal tip 24. Moreover, the multi-lumen construct of the distal tip 24 may provide improved torsional transmission from the shaft 22 to the carrier arm 28 while maintaining the structural integrity of both the shaft 22 and the carrier arm 28 where they couple to the distal tip 24.

The medical device 12 may include a cooling assembly positionable about the electrodes 26 to reduce and/or regulate a temperature of the electrodes 26 and/or a tissue region interacting with the electrodes 26. The cooling assembly may deliver fluid from a proximal portion of the device 12 to the distal portion 20 of the medical device 12 to affect the temperature of the electrodes 26 by either dispersing or irrigating the electrodes 26 with a cooling fluid or by cooling at least a portion of the carrier arm 28 and/or electrodes 26 through conduction in the absence of direct fluid dispersion or irrigation.

For example, the cooling assembly may include a fluid conduit 30 coupled to the distal portion 20 of the medical device 12. The fluid conduit 30 may define a lumen therein for the passage or delivery of a fluid from the proximal portion of the elongate body 16 and/or the control unit 14 to the distal portion 20 of the medical device 12. The fluid conduit 30 may further include one or more apertures or openings 32 therein to provide for the dispersion or directed ejection of fluid from the lumen to an environment exterior to the fluid conduit 30 and/or the electrodes 26. The fluid conduit 30 may be flexible, constructed from a shape memory material (such as Nitinol), and/or include other controllably deformable materials that allow the fluid conduit 30 to be manipulated into a plurality of different geometric configurations, shapes, and/or dimensions. For example, the fluid conduit 30 may be oriented or deployed into a substantially linear configuration, a partial looped or circular configuration, and/or a substantially helical configuration. The geometrical configuration of the fluid conduit 30 may be manipulated to mirror or align with a selected configuration of the carrier arm 28 and the electrodes 26 for more efficient fluid dispersion and resulting temperature control, for example.

Figure 1C:
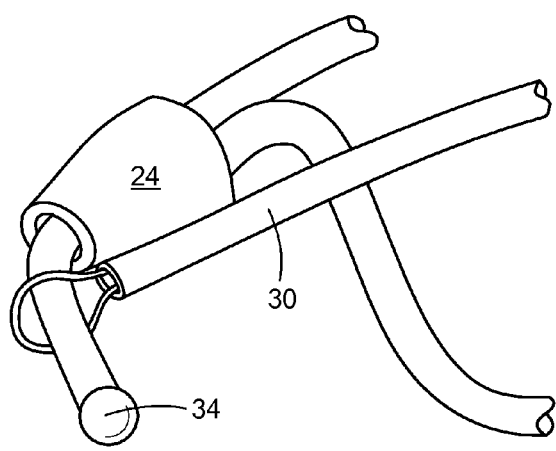
FIG. 1C is an alternative view of the system of FIG. 1A.

The cooling assembly may be coupled to or otherwise extend from the elongate body 16, and may further be coupled to the shaft 22 and/or distal tip 24 of the medical device 12. The cooling assembly may be releasably engageable with the distal portion 20 and/or the elongate body 16 to allow selectively implementation and operation of the cooling assembly in some procedures or applications, while not in others. For example, as shown in FIGS. 1A-1C, the fluid conduit 30 may be coupled to the distal tip 24 and/or a guide wire 34 extending from the distal tip 24. A proximal portion of the fluid conduit 30 may be coupled to an exterior, proximal portion of the elongate body 16 (not shown). The fluid conduit 30 may be manipulated into substantially the same configuration as the carrier arm 28, such as a helical, coiled configuration as shown in FIGS. 1A-1C. The similar geometric configuration allows fluid dispersion from the apertures 32 in the fluid conduit 30 to be directed closely to the electrodes 26.

Figure 2A:
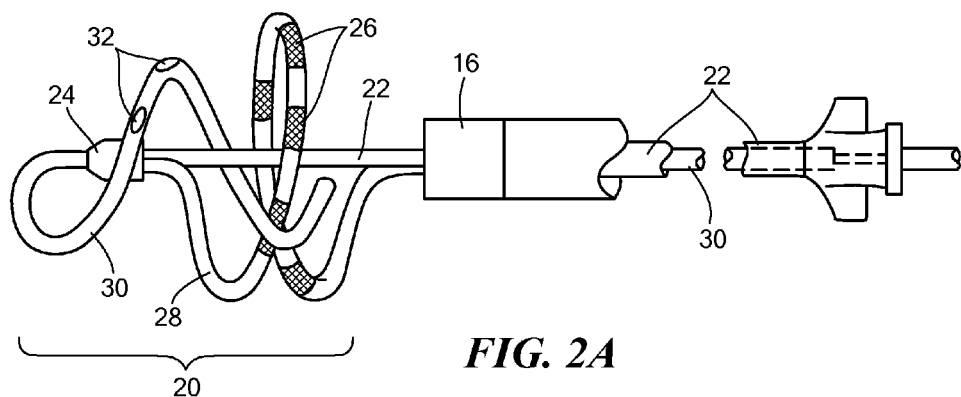
FIG. 2A is an illustration of another example of a medical system constructed in accordance with the principles of the present invention.
Figure 2B:
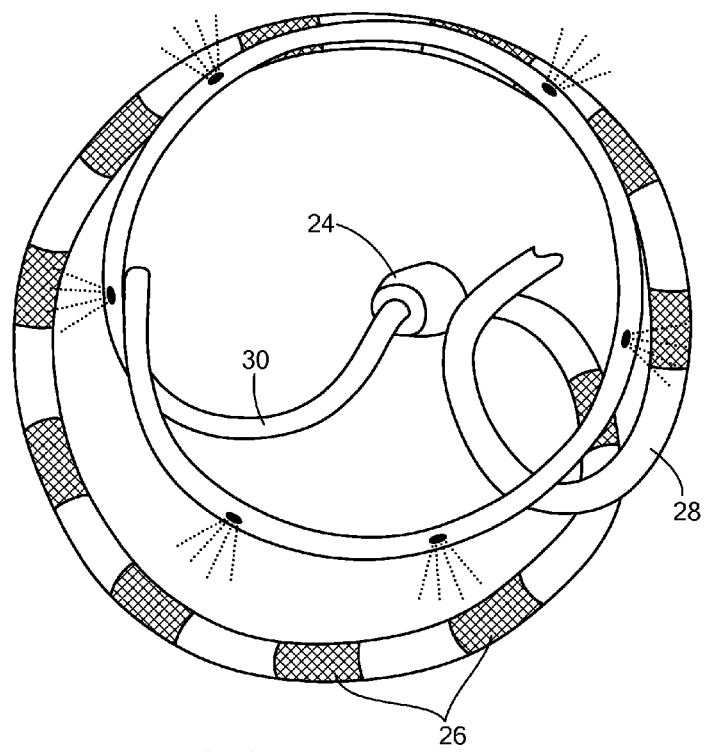
FIG. 2B is an alternative view of the system of FIG. 2A.
Figure 2C:
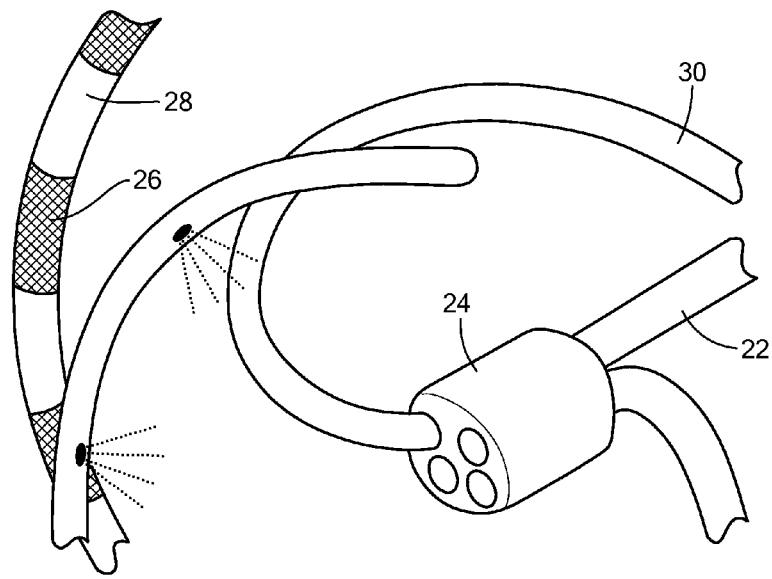
FIG. 2C is an alternative view of the system of FIG. 2A.

Turning now to FIGS. 2A-2C, the fluid conduit 30 may extend through an interior segment of the elongate body 16 and the shaft 22. The fluid conduit 30 may exit through the distal tip 24 and extend in a proximal direction towards the carrier arm 28 and the electrodes 26 thereon. The fluid conduit 30 may be movable within the elongate body through a guide wire lumen defined therein. The fluid conduit 30 may be exchangeable with a guide wire to alternate between steering or directing the medical device 12 to a desired locale and delivering fluid to the electrodes 26 during an operative duration of a designated procedure. The fluid conduit 30 may extend to a proximal portion of the medical device and terminate at a coupling or luer that is connectable to a fluid source and/or the control unit 14.

Figure 3A:
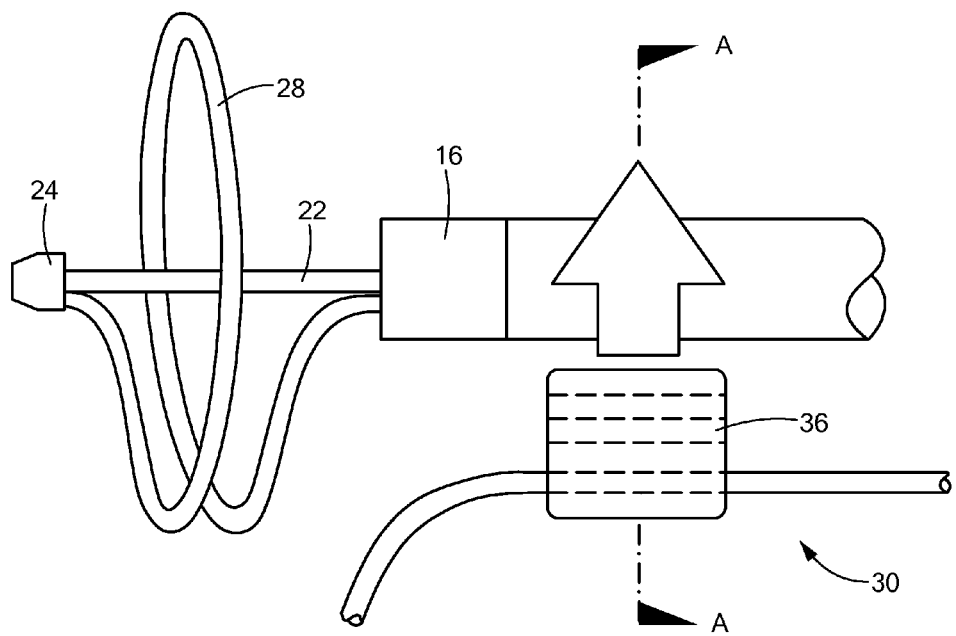
FIG. 3A is an illustration of another example of a medical system constructed in accordance with the principles of the present invention.
Figure 3B:
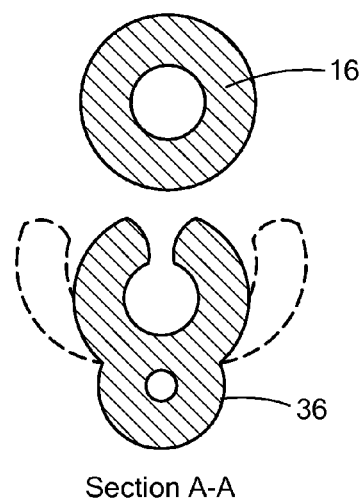
FIG. 3B is a cross-sectional view of the system of FIG. 3A.
Figure 3C:
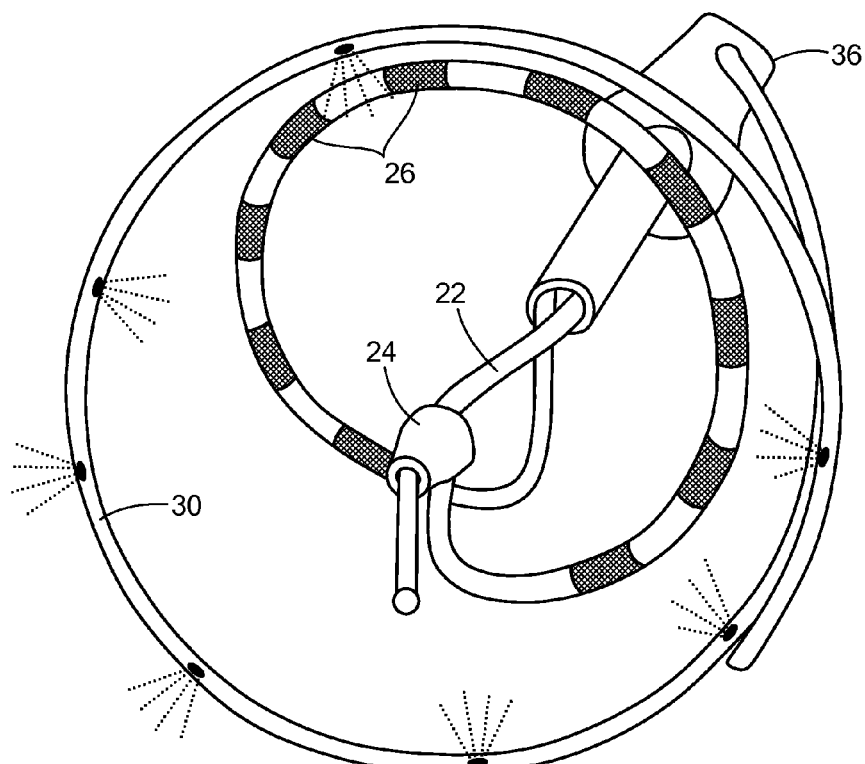
FIG. 3C is an alternative view of the system of FIG. 3A.

Referring now to FIGS. 3A-3C, the fluid conduit 30 may be releasably attached to the elongate body 16 towards the distal portion 20 by a connector 36. The connector may generally define a lumen or hole that the fluid conduit 30 may be placed through, while also defining a "U" or "C"-shaped portion to engage the elongate body 16.

Figure 4A:
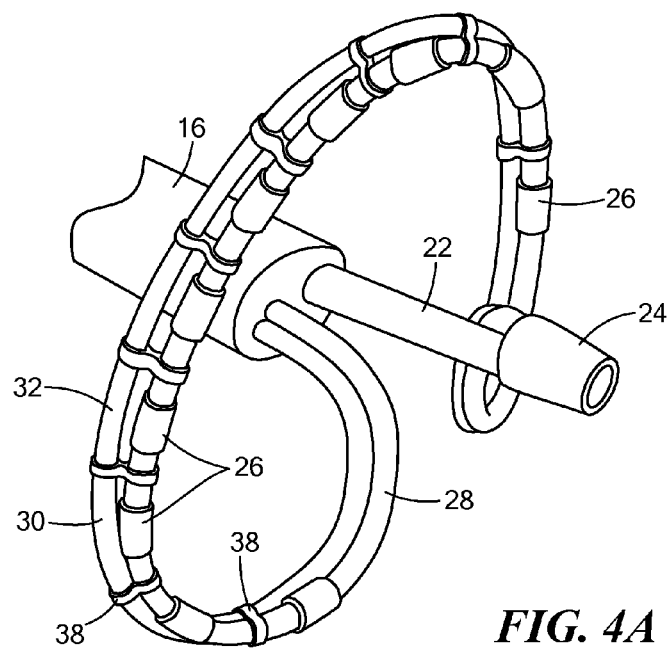
FIG. 4A is an illustration of another example of a medical system constructed in accordance with the principles of the present invention.
Figure 4B:
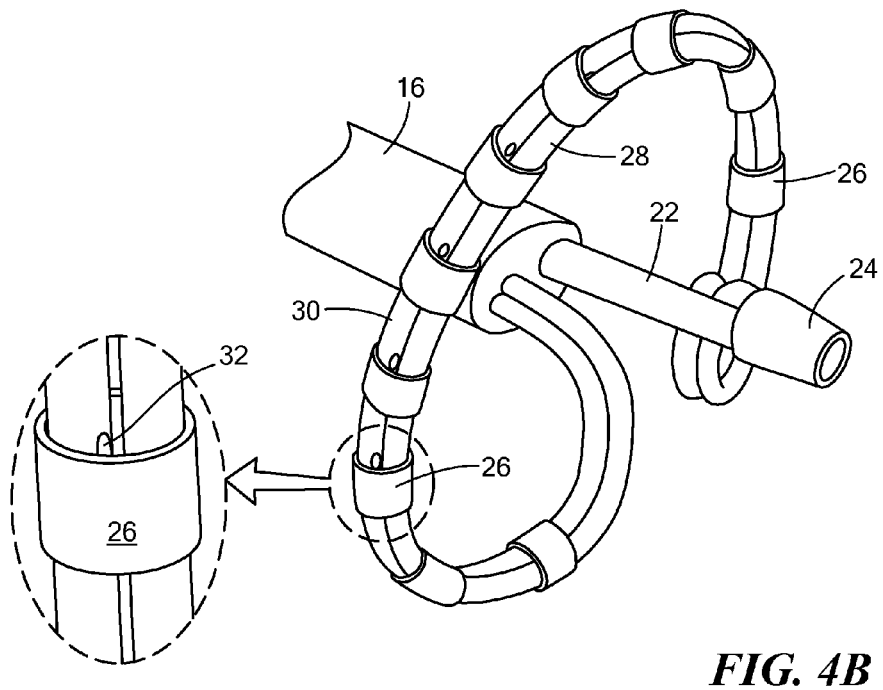
FIG. 4B is an illustration of another example of a medical system constructed in accordance with the principles of the present invention.
Figure 4C:
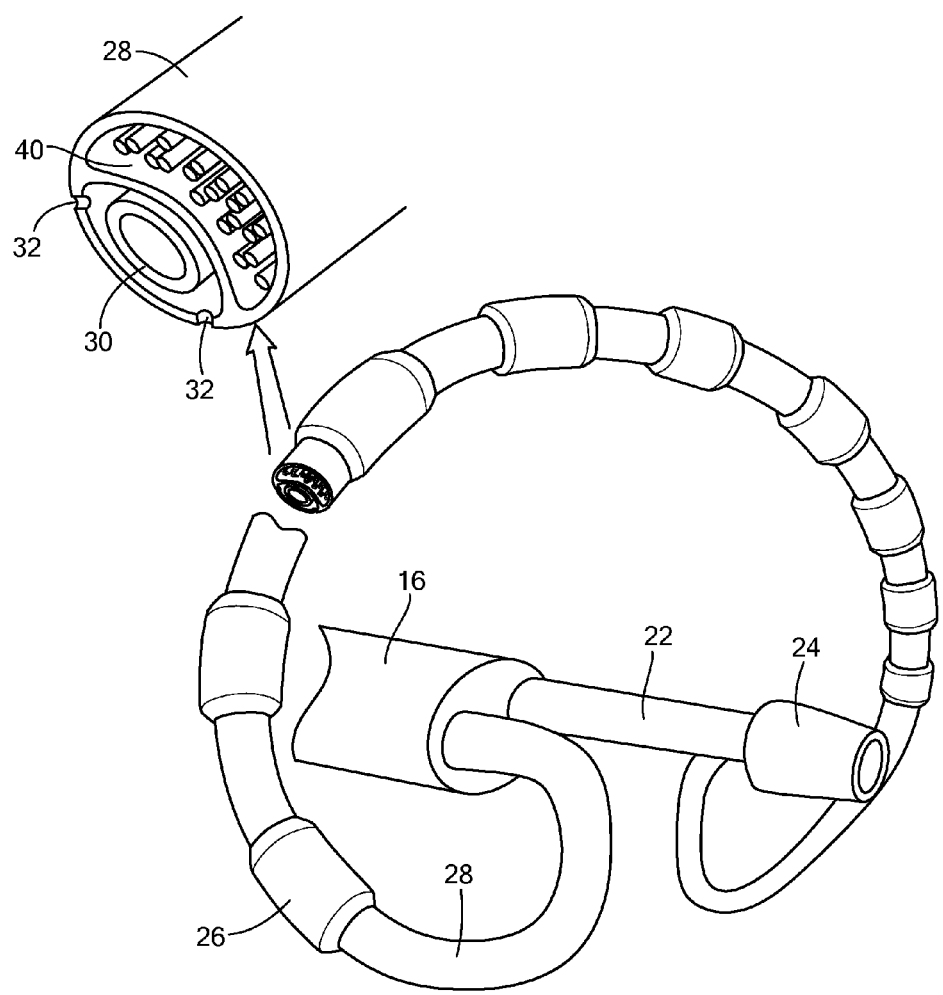
FIG. 4C is an illustration of another example of a medical system constructed in accordance with the principles of the present invention.

Turning now to FIGS. 4A-4C, the fluid conduit 30 may extend through an interior of the elongate body 16 and be coupled directly to the carrier arm 28 at the distal portion 20 of the medical device 12. The fluid conduit 30 may extend adjacent to carrier arm 28 along substantially the entire length of the carrier arm 28, with both the fluid conduit 30 and the carrier arm 28 coupling to the distal tip 24. Coupling the fluid conduit 30 and the carrier arm 28 together allows the two components to be manipulated in desired positions and geometric configurations as a single unit, rather than through independent manipulation and positioning of the other examples described herein. The coupling may include locating the apertures 32 directly adjacent to the electrodes 26. The coupling of the fluid conduit 30 to the carrier arm 28 may be accomplished using a plurality of connectors 38 as shown in FIG. 4A, or the electrodes 26 themselves may circumscribe or extend around both the fluid conduit 30 and the carrier arm 28 to join the two together, as shown in FIG. 4B. Alternatively, the fluid conduit 30 may be disposed within the carrier arm 28, as shown in FIG. 4C, where the carrier arm 28 defines an interior lumen for passage of the fluid conduit 30 as well as apertures 32 therein for dispersion of a fluid. The carrier arm 28 may define a secondary lumen 40 for routing wires or the like to the electrodes 26 and/or sensors of the carrier arm 28 without exposing the second lumen to fluid flow, which could cause an electrical short.

Figure 5A:
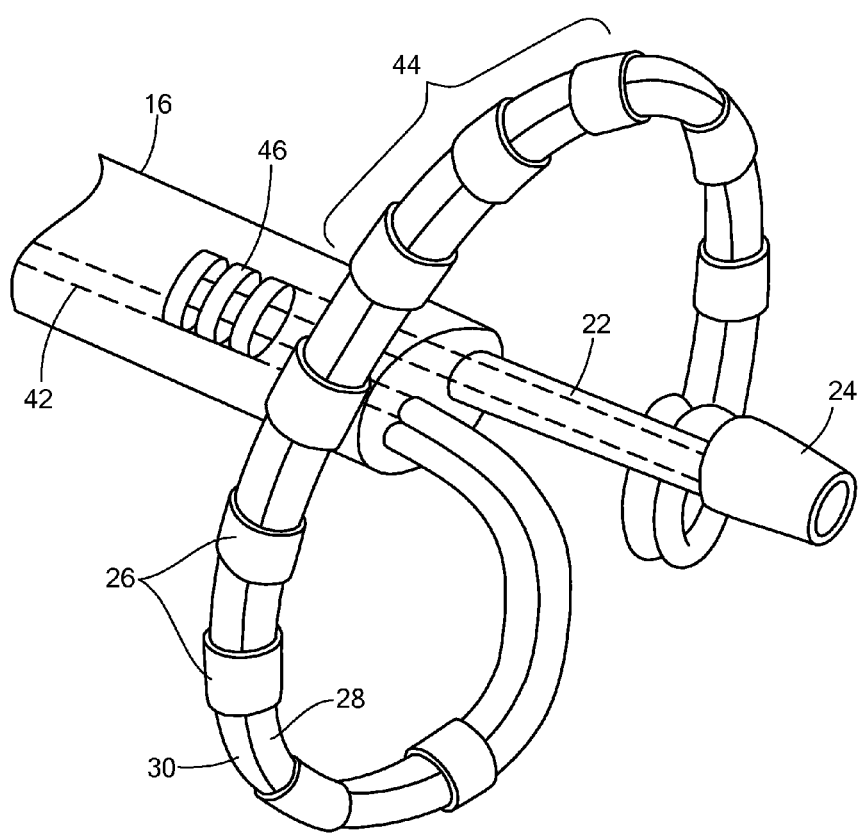
FIG. 5A is an illustration of another example of a medical system constructed in accordance with the principles of the present invention.
Figure 5B:
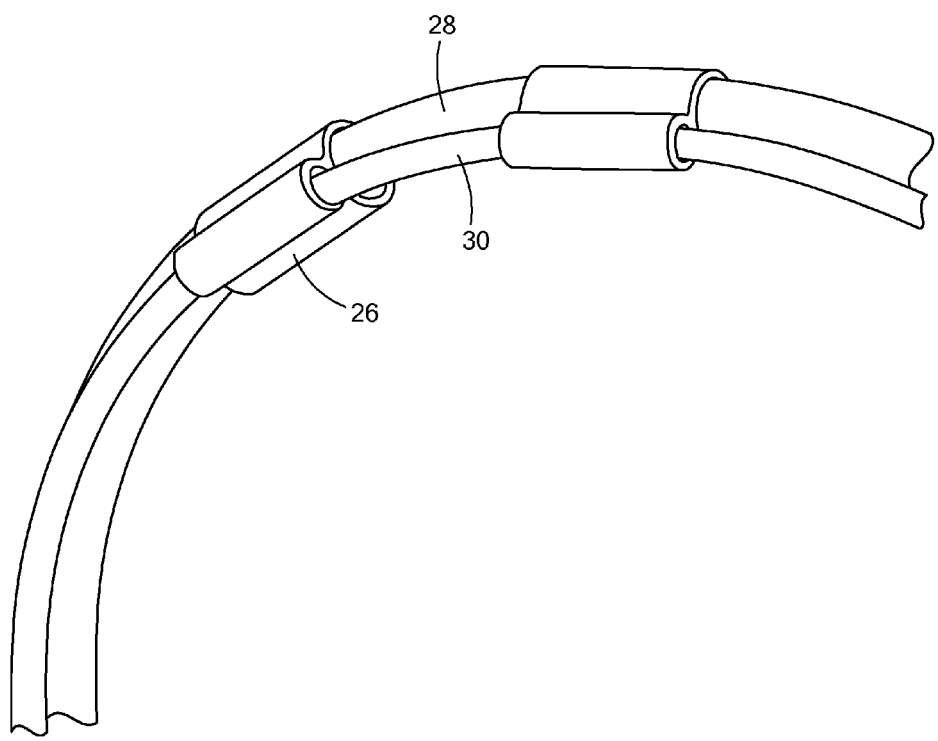
FIG. 5B is an illustration of another example of a medical system constructed in accordance with the principles of the present invention.

Referring now to FIGS. 5A and 5B, the cooling assembly may regulate or control temperature of the carrier arm 28 and/or electrodes 26 without direct fluid dispersion or irrigation at the distal portion 20 or tissue site. For example, the fluid conduit 30 may be at least partially disposed within the elongate body 16 and may also extend from the elongate body 16 or otherwise be exposed at the distal portion 20 of the medical device 12. The fluid conduit may define or include a first segment 42 disposed within the elongate body 16. The first segment 42 may course along a substantial length of the elongate body 16 and be connectable or otherwise placed into communication with the control unit 14. The fluid conduit 30 may also include or define a second segment 44 extending from the elongate body 16 at the distal portion 20 and coupled to the carrier arm 28. The second segment 44 may have a substantially continuous, thermally-conductive region for thermal transfer with the electrodes 26 and/or the carrier arm 28. The fluid conduit 30 may also include or define a third segment 46 that is adjacent or in proximity to the first segment of 42 of the fluid conduit, where the third segment 46 includes or defines one or more openings positioned to dispense or otherwise deliver fluid from within the third segment 46 onto an exterior surface or portion of the first segment 42. For example, as shown in FIG. 5A, the third segment 46 may be at least partially disposed within the elongate body 16 and oriented substantially parallel to the first segment 42 of the fluid conduit. The third segment 46 may include one or more coils or windings that circumscribe or otherwise wrap around a portion of the first segment 42, where the openings are on an interior-facing surface of the windings to direct fluid onto the first segment 42. The windings 32 may be contained within a portion of the elongate body 16, and may be movable and/or slidable with respect to the elongate body 16 other portions of the fluid conduit 30. The windings may include one or more of the openings to disperse coolant or a fluid onto the first segment 42 of the fluid conduit 30, where the dispersed coolant or fluid reduces the temperature of the first segment 42 and fluid flowing through it which, in turn, reduces the temperature of the second segment 44, thus allowing it to cool or thermally regulate the carrier arm 28 and/or the electrodes 26. The fluid conduit 30 thus provides a closed-loop circulation path within the medical device 12 without dispersing or distributing fluid directly onto a tissue site or into the surrounding environment.

Similar to the configuration in FIG. 4B, the second segment 44 of the fluid conduit 30 may be coupled to the carrier arm 28 by the electrodes 26 themselves. The electrodes 26 may have a ring-like form to circumscribe both the second segment 44 and the carrier arm 28, or alternatively, as shown in FIG. 5B, the electrodes may define a "Figure-8" cross section facilitating engagement of the second segment 44 and the carrier arm 28.

The medical device 12 may further include an exhaust lumen or conduit providing an evacuation path for fluid dispersed or otherwise present within the medical device 12. The exhaust lumen may be defined by a wall of the elongate body 16 itself, or by another auxiliary tube or conduit disposed within at least a portion of the medical device 12. The exhaust lumen may be in fluid communication with a proximal portion of the elongate body 16 and/or the medical device 12 to allow access and/or coupling of the exhaust lumen to the control unit 14 for removal, storage, and/or recirculation of a fluid exiting the exhaust lumen. The exhaust lumen and the fluid conduit 30 may thus provide a fluid flow path through at least a portion of the medical device 12.

Referring again to FIG. 1, the medical device 12 may include a handle 48 coupled to the proximal portion of the elongate body 16. The handle 48 can include circuitry for identification and/or use in controlling of the medical device 12 or another component of the system 10. Additionally, the handle 48 may be provided with a fitting 50 for receiving a guide wire or another diagnostic/treatment instrument (not shown). The handle 48 may also include connectors 52 that are matable to the control unit 14 to establish communication between the medical device 12 and one or more components or portions of the control unit 14.

The handle 48 may also include one or more actuation or control features that allow a user to control, deflect, steer, or otherwise manipulate a distal portion of the medical device 12 from the proximal portion of the medical device 12. For example, the handle 48 may include one or more components such as a lever or knob 54 for manipulating the elongate body 16 and/or additional components of the medical device 12. For example, a pull wire 56 with a proximal end and a distal end may have its distal end anchored to the elongate body 16 at or near the distal portion 20. The proximal end of the pull wire 56 may be anchored to an element such as a cam in communication with and responsive to the lever 54.

The medical device 12 may include an actuator element 58 that is movably coupled to the proximal portion of the elongate body 16 and/or the handle 48 for the manipulation and movement of a portion of the medical device 12, such as the fluid conduit 30, shaft 22, and/or distal portion 20, for example. The actuator element 58 may include a thumb-slide, a push-button, a rotating lever, or other mechanical structure for providing a movable coupling to the elongate body 16 and/or the handle 48. Moreover, the actuator element 58 may be movably coupled to the handle 48 such that the actuator element 58 is movable into individual, distinct positions, and is able to be releasably secured in any one of the distinct positions.

Where the fluid conduit 30 and the carrier arm 28 are coupled to the shaft 22, movement of the shaft 22 allows the controllable transition of the fluid conduit 30 and/or the carrier arm 28 from one geometric shape, configuration, or dimension to another. By sliding and rotating the shaft 22, through manipulation of the actuator element 58 for example, fluid conduit 30 and/or the carrier arm 28 can be manipulated into various geometries for the desired clinical or therapeutic effect.

The system 10 may include one or more treatment or diagnostic sources coupled to the medical device 12 for use in an operative procedure, such as tissue ablation, for example. The control unit 14 may include a fluid supply 60 including a coolant, cryogenic refrigerant, saline, or the like, an exhaust or scavenging system (not shown) for recovering or venting expended fluid for re-use or disposal, as well as various control mechanisms. In addition to providing an exhaust function for the fluid or coolant supply, the control unit 14 may also include pumps, valves, controllers or the like to recover and/or re-circulate fluid delivered from the fluid supply 60 to the handle 48, the elongate body 16, and/or the fluid pathway(s) of the medical device 12. A vacuum pump 62 in the control unit 14 may create a low-pressure environment in one or more conduits within the medical device 12, such as the exhaust lumen, so that fluid is drawn into the conduit(s)/lumen(s) of the elongate body 16, away from the distal portion 20 and towards the proximal portion 18 of the elongate body 16.

The console 12 may also include a radiofrequency signal generator or electrical power source 64 in electrical communication with the electrodes 26. The generator 64 may include a plurality of output channels, with each channel coupled to an individual electrode or electrically conductive surface of the medical device 12. The generator 64 may be operable in one or more modes of operation, including for example: (i) bipolar energy delivery between at least two electrodes 26 or electrically-conductive portions of the medical device 12 within a patient's body, (ii) monopolar or unipolar energy delivery to one or more of the electrodes 26 or electrically-conductive portions on the medical device 12 within a patient's body and through a patient return or ground electrode (not shown) spaced apart from the electrodes 26 of the medical device 12, such as on a patient's skin for example, and (iii) a combination of the monopolar and bipolar modes.

While monopolar and bipolar RF ablation energy may be the selected forms of energy to pass through the electrodes of the medical device, other forms of ablation energy may be additionally or alternatively emitted from the treatment assembly, including electrical energy, electroporation energy, magnetic energy, microwave energy, thermal energy (including heat and cryogenic energy) and combinations thereof. Moreover, other forms of energy that may be applied can include acoustic energy, sound energy, chemical energy, photonic energy, mechanical energy, physical energy, radiation energy and a combination thereof.

The system 10 may further include one or more sensors to monitor the operating parameters throughout the system 10, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/ fluid paths of the medical device 12. Such valves, controllers, or the like may be located in a portion of the medical device 12 and/or in the control unit 14. The control unit 14 may include one or more controllers, processors, and/or software modules containing instructions or algorithms to provide for the automated operation and performance of the features, sequences, calculations, or procedures described herein.

In a particular example, the generator 64 may be configured to generate and control the delivery of energy based on temperature feedback from a respective thermocouple or sensor in proximity to one or more electrodes 26. Each electrode 26 may be independently monitored followed by temperature-controlled delivery of energy. Energy delivery may further automatically be duty-cycled to maximize the delivery of energy to the electrode based on the measured tissue temperature. Hence, as the tissue temperature increases due to delivery of energy (resistive heating), the electrodes 26 in turn increase in temperature, as monitored by the corresponding thermocouple. For instance, during bipolar delivery, if the set target temperature of the electrodes is 60° C. and one of the two electrodes is monitored at 55° C., while the other electrode is monitored to be at 50° C., the generator 64 will selectively limit energy delivery based on the needs of one electrode measured at 55° C. This prevents either electrode of the pair from ever significantly surpassing the set target temperature. In contrast, during a monopolar phase of the energy delivery, the signal generator 64 will deliver energy to each electrode 26 solely based on the temperature measured by its corresponding thermocouple. The temperature measurements may be performed between duty cycles (off-cycles) to minimize interference and to optimize accuracy of temperature readings.

In an exemplary method of use, the medical system 10 may be used to deliver therapeutic treatment, such as ablation treatment for example, to a targeted tissue area, which may include a targeted tissue region in the heart, a tumor, or other diagnosed region slated for treatment. The distal portion 20 may be positioned in the proximity of the targeted tissue area and the carrier arm 28 and/or fluid conduit 30 may be manipulated into the desired geometric configuration, whether circular, arcuate, linear, or the like. Such positioning and manipulation may be aided or facilitated by visualization methods including fluoroscopy or the like as known in the art. Once the medical device 12 is positioned in the desired location, the system 10 may be operated to thermally affect the targeted tissue.

For example, the electrodes 26 may deliver radiofrequency energy treatment to the targeted tissue to achieve the desired therapeutic effect, such as the controlled ablation of problematic tissue to an effective depth within the targeted tissue region. Powering of the electrodes 26 may include delivery of a radiofrequency signal or current form the radiofrequency generator 64 resulting in a current flow, and thus heating, between one or more of the electrodes either between each other (e.g., bipolar RF delivery) or to a ground/patient electrode (not shown) in unipolar or monopolar operation. The electrodes 26 may be powered ablate or otherwise treat tissue until a preselected temperature or power delivery threshold has been reached. The predefined temperature or power delivery threshold may be selected to ensure that the affected tissue is not charred or otherwise heated to an undesirable degree.

In addition, a fluid or coolant may be introduced into the fluid conduit 30 of the medical device 12 to aid in regulating or controlling a temperature of the tissue site and/or electrodes 26. In particular, coolant may be transferred from the fluid source 60 in the control unit 14 to the fluid conduit 30. The fluid may be dispersed into the treatment area through the apertures 32 or may be routed through the device in a closed-loop fashion for thermal transfer through conduction. The fluid flow through the fluid conduit 30 of the medical device 12 may be intermittently provided in pulsed flow, or may be continuously circulated throughout the segments of the conduit 30. Further, the control unit 14 may modulate fluid flow by varying pressure, flow rates, or the like in direct response to the measured temperatures in the distal portion 20 as relayed by temperature sensors. For example, upon reaching a preselected temperature threshold or range at the tissue interface, fluid flow through the fluid flow path may be increased or decreased accordingly to substantially maintain a target temperature at the distal portion 20 of the device 12. The fluid flow may be conducted simultaneously and/or in alternating sequence with energy delivery to the electrodes 26.

It will be appreciated by persons skilled in the art that the present invention is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention. A variety of modifications and variations are possible in light of the above teachings without departing from the scope and spirit of the invention, which is limited only by the following claims.

What is claimed is:

1. A medical device, comprising:
   a catheter body;
   a carrier arm coupled to the catheter body, the carrier arm including a plurality of electrodes and being transitionable from a substantially linear configuration to a substantially helical configuration; and
   a fluid conduit coupled to the catheter body, the fluid conduit being spaced apart from the carrier arm and being transitionable from a substantially linear configuration to a substantially helical configuration independently of the carrier arm.

2. The medical device of claim 1, wherein the fluid conduit is releasably coupled to the catheter body.

3. The medical device of claim 1, wherein the fluid conduit includes a plurality of apertures.

4. The medical device of claim 1, wherein the fluid conduit is attached to the carrier arm by a plurality of connectors.

5. The medical device of claim 4, wherein the plurality of connectors are thermally conductive.

6. The medical device of claim 1, further comprising a shaft movably coupled to the catheter body, wherein a proximal portion of the carrier arm is attached to the catheter body and a distal portion of the carrier arm is attached to the shaft.

7. The medical device of claim 6, wherein a proximal portion of the fluid conduit is attached to the catheter body and a distal portion of the fluid conduit is attached to the shaft.

8. The medical device of claim 6, wherein the fluid conduit extends from a distal end of the shaft.

9. The medical device of claim 1, further comprising a fluid supply in fluid communication with the fluid conduit.

10. The medical device of claim 1, further comprising a radiofrequency signal generator in communication with the plurality of electrodes.

11. A medical device, comprising:
a catheter body;
a carrier arm coupled to the catheter body, the carrier arm being transitionable from a substantially linear configuration to a substantially helical configuration;
a fluid conduit extending adjacent to the carrier arm along substantially the entire length of the carrier arm; and
a plurality of electrodes, each of the plurality of electrodes being disposed about both the carrier arm and the fluid conduit.

12. The medical device of claim 11, wherein the fluid conduit defines a plurality of apertures, each aperture positioned proximate to each of the plurality of electrodes.

13. The medical device of claim 11, wherein each electrode defines a single passage therethrough.

14. The medical device of claim 11, wherein each electrode defines a plurality of passages therethrough.

15. The medical device of claim 11, wherein the fluid conduit defines a first portion and a second portion, wherein the second portion is coiled around the first portion.

16. The medical device of claim 11, wherein the fluid conduit defines a first portion and a second portion, wherein the second portion defines a plurality of openings positioned to disperse fluid onto the first portion.

* * * * *